United States Patent
Koseki et al.

(10) Patent No.: US 11,014,865 B2
(45) Date of Patent: May 25, 2021

(54) PRODUCTION METHOD FOR CYCLOPENTENONE DERIVATIVE

(71) Applicants: Tohoku University, Miyagi (JP); Genesis Research Institute, Inc., Aichi (JP)

(72) Inventors: Yoshitaka Koseki, Miyagi (JP); Hitoshi Kasai, Miyagi (JP); Takaaki Kamishima, Aichi (JP)

(73) Assignees: Tohoku University, Miyagi (JP); Genesis Research Institute, Inc., Aichi (JP)

( * ) Notice: Subject to any disclaimer, the term of this patent is extended or adjusted under 35 U.S.C. 154(b) by 0 days.

(21) Appl. No.: 16/968,096

(22) PCT Filed: Feb. 12, 2019

(86) PCT No.: PCT/JP2019/004796
§ 371 (c)(1),
(2) Date: Aug. 6, 2020

(87) PCT Pub. No.: WO2019/159871
PCT Pub. Date: Aug. 22, 2019

(65) Prior Publication Data
US 2021/0024444 A1 Jan. 28, 2021

(30) Foreign Application Priority Data
Feb. 13, 2018 (JP) .............................. JP2018-022867

(51) Int. Cl.
*C07C 45/00* (2006.01)
*C07C 49/00* (2006.01)
*C07C 49/537* (2006.01)

(52) U.S. Cl.
CPC .................................. *C07C 49/537* (2013.01)

(58) Field of Classification Search
CPC ...... C07C 45/51; C07C 45/511; C07C 49/537
See application file for complete search history.

(56) References Cited

U.S. PATENT DOCUMENTS
5,776,984 A 7/1998 Dellaria et al.

FOREIGN PATENT DOCUMENTS
JP 2014-73987 A 4/2014

OTHER PUBLICATIONS

Elliott, J.D. et al., "Studies related to cyclopentanoid natural products. Part 1. Preparation of (4RS)- and (4R)-4-hydroxy-2-hydroxymethylcyclopent-2-en-1-one; a versatile synthetic intermediate", J. Chem. Soc., Perkin Trans. 1, 1981, 1782-1789.

*Primary Examiner* — Sikarl A Witherspoon
(74) *Attorney, Agent, or Firm* — Gavrilovich, Dodd & Lindsey LLP

(57) ABSTRACT

[Problem]
The present invention provides an industrially-preferable, cost-efficient, low-cost production method for 4-hydroxy-2-hydroxymethyl-2-cyclopenten-1-one (a compound represented by formula (I)) useful as a medicine, an agricultural chemical, or a raw material or intermediate of a medicine, an agricultural chemical, or the like.
[Solution]
According to the present invention, this compound represented by formula (I) is produced by subjecting an easily available compound represented by formula (II) (tri-O-acetyl-D-glucal) to a heating reaction in pressurized water.

6 Claims, No Drawings

PRODUCTION METHOD FOR CYCLOPENTENONE DERIVATIVE

CROSS REFERENCE TO RELATED APPLICATIONS

This application is a U.S. National Phase Application filed under 35 U.S.C. § 371 and claims priority to International Application No. PCT/JP2019/004796, filed Feb. 12, 2019, which application claims priority to Japanese Application No. 2018-022867, filed Feb. 13, 2018, the disclosures of which are incorporated herein by reference.

TECHNICAL FIELD

The present invention relates to a production method for 4-hydroxy-2-hydroxymethyl-2-cyclopenten-1-one.

TECHNICAL BACKGROUND 4-hydroxy-2-hydroxymethyl-2-cyclopenten-1-one as represented by formula (I) is considered to be a desired synthetic block for pharmaceutical raw materials such as pentenomycin and vertimycin. Its production method has already been reported in a document (Non-Patent Document 1).

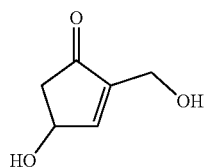

(I)

In Non-Patent Document 1, a production method for the (4RS) form of formula (I) using chloroacetaldehyde and ethyl acetoacetate as raw materials and a production method for the (4R) form of formula (I) using quinic acid as a raw material are disclosed. In the production method using chloroacetaldehyde and ethyl acetoacetate, chloroacetaldehyde reacts with ethyl acetoacetate to produce a furan derivative (ethyl 2-methyl-3-furancarboxylate, yield: 66%). The furan derivative is reduced with lithium aluminum hydride to 3-hydroxymethyl-2-methylfuran. After purification with silica gel column chromatography (yield of 3-hydroxymethyl-2-methylfuran: 52%), it is converted to a dihydrofuran derivative (2,5-dihydro-3-hydroxymethyl-2,5-dimethoxy-2-methylfuran, yield: 80%) by reaction in methanol-ether solution (containing bromine) and addition of trimethylamine. The dihydrofuran derivative causes a ring-opening reaction of the furan ring and an intramolecular aldol reaction in an aqueous solution of dioxane (containing hydroquinone) whose pH is adjusted with a solution of phosphate buffer to produce a cyclopentenone derivative represented by the above formula (I) (the yield after solvent extraction and purification with silica gel column chromatography: 50%). The overall yield of the cyclopentenone derivative after the five reaction steps is about 14%.

It has been reported in Patent Document 1 that 4-hydroxy-2-hydroxymethyl-2-cyclopenten-1-one can be obtained by chemical conversion reaction in the step of heating (in the range of 150° C. to 300° C.) an aqueous solution of 2-deoxy-aldohexose as a starting material without evaporation. However, 2-deoxy-aldohexose including 2-deoxyglucose as a raw material is very expensive. In addition, problems remain regarding the yield of converting 2-deoxy-aldohexose to 4-hydroxy-2-hydroxymethyl-2-cyclopenten-1-one and ease of purification of 4-hydroxy-2-hydroxymethyl-2-cyclopenten-1-one as the desired product. Accordingly, there is room for improvement in highly economical industrial production.

It is industrially desirable that in replace of 2-deoxy-aldohexose, the cyclopentenone derivative represented by formula (I) is directly produced from an inexpensive aldohexose or a derivative thereof. However, almost no production method has been proposed so far.

PRIOR ART DOCUMENTS

Patent Document

1. U.S. Pat. No. 5,776,984

Non-Patent Document

1. J. D. Elliott, et al., J. Chem. Soc. Perkin Trans. I, 1782 (1981)

SUMMARY OF THE INVENTION

Problems to be Solved by the Invention

There had been a demand for an industrially preferable production method for the compound of the above formula (I) as the desired product, which can solve one or more problems in the above-mentioned conventional techniques. Accordingly, an objective of the present invention is to provide an inexpensive production method for the desired product which is industrially preferable and economical.

Means for Solving the Problems

In view of the above situation, the present inventor has diligently studied the production method for the compound of the above formula (I). As a result, it has been found that the above problems can be solved by providing the following production method for the compound of the above formula (I). The present inventor has completed the present invention based on this finding.

That is, the present invention is as follows.

[1] A production method for the compound represented by formula (I) using the compound represented by formula (II) as a starting material.

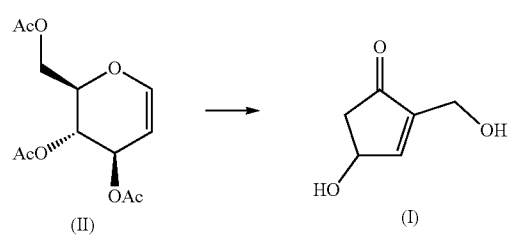 [SMILES: CC(=O)OC[C@H]1OC=C[C@@H](OC(C)=O)[C@@H]1OC(C)=O ; O=C1CC(O)C=C1CO ; "(I)" ; "(II)"]

[2] The production method according to [1], which is characterized by comprising a step of heating an aqueous solution of the compound represented by formula (II) at 100 to 250° C. in a pressurized state without evaporation.

[3] A production method for the compound represented by formula (I) using the compound represented by formula (III) as a starting material.

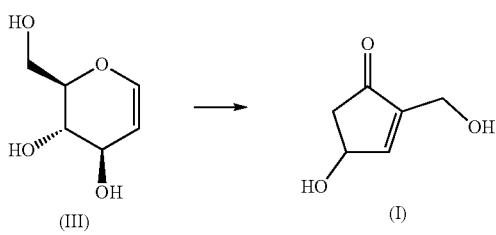 [SMILES: OC[C@H]1OC=C[C@@H](O)[C@@H]1O ; O=C1CC(O)C=C1CO ; "(III)" ; "(I)"]

[4] The production method according to [3], which is characterized by comprising a step of heating an aqueous solution of the compound represented by formula (III) at 100 to 250° C. in a pressurized state without evaporation.
[5] The production method according to [2], wherein the concentration of the compound represented by formula (II) is in the range of 0.1 to 1.0M.
[6] The production method according to [2], wherein the pH of the aqueous solution of the compound represented by formula (II) is in the range of 4 to 9.
[7] The production method according to [4], wherein the concentration of the compound represented by formula (III) is in the range of 0.1 to 1.0M.
[8] The production method according to [4], wherein the pH of the aqueous solution of the compound represented by formula (III) is in the range of 4 to 9.

Effects of the Invention

A novel and industrially applicable production method for the compound of the above formula (I) as the desired product is provided by the present invention. According to the invention, an industrially preferable production method for the compound of the above formula (I) as the desired product, capable of solving one or more problems in the above-mentioned conventional techniques is provided. According to the invention, producing 4-hydroxy-2-hydroxymethyl-2-cyclopenten-1-one using D-glucose, which is cheaper (about several hundred yen/kg) and is also a biomass resource, leads to inexpensive production of bioactive compounds such as prostaglandins. The present invention relates to a simple production technology of 4-hydroxy-2-hydroxymethyl-2-cyclopenten-1-one using inexpensive and constantly available D-glucose as a raw material. The compound is a precursor of prostaglandins, so that inexpensive and rapid supply is possible. Therefore, the method of the present invention is industrially preferable, economical, and has high industrial utility value.

EMBODIMENTS FOR CARRYING OUT THE INVENTION

Hereinafter, the embodiments of the present invention will be described. These embodiments are just examples for carrying out the invention. The present invention is not limited to these embodiments.
Hereinafter, a production method for the cyclopentenone derivative represented by formula (I) according to the present invention will be described.
(Starting Materials)
Examples of aldohexose as starting materials include D-glucose, L-glucose, D-galactose, L-galactose, D-gulose, L-gulose, D-allose, L-allose and the like.
The aldohexose as starting materials, may have a pyranose ring structure or a cyclic isomer structure of a furanose ring structure. Besides, in these cases, it may have either α-type or δ-type of anomeric isomer structure, or a mixture thereof.
The compound of formula (II) (tri-O-acetyl-D-glucal) as a starting material is itself a commercial product. Alternatively, it can be easily obtained from glucose in one step according to well-known technology (for example, Synthesis 48, 1069, 2016).
The compound of formula (III) (D-glucal) as a starting material is itself a commercial product. Alternatively, it can be easily obtained according to well-known technology (for example, Organic Letters 13, 4394, 2011).
A method for converting the compound of formula (II) or the compound of formula (III) into the cyclopentenone derivative represented by formula (I) will be described.

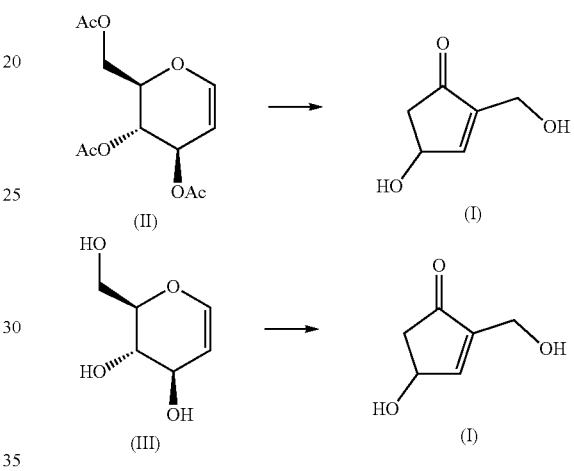

(Reaction Solvents)
Examples of water used as a reaction solvent include tap water, pure water such as ion-exchanged water, and ultrapure water. However, in order to improve the yield of the product, it is preferable to use pure water such as ion-exchanged water or ultrapure water which contain few impurities. In order to prevent an oxidation reaction due to oxygen contained in the air, it is more preferable to use degassed ion-exchanged water and ultrapure water. The pH of water is preferably in the range of 4 to 8, which is weakly acidic to near neutral. Under strong acidic or alkaline conditions, side reactions may proceed further, and the yield of the desired compound of formula (I) may decrease. When tap water is used at a high temperature, a trace amount of compounds (calcium carbonate, silica gel, etc.) contained in the tap water may generate scales in reaction devices. Accordingly, the devices need to be inspected.
(Amount of Solvents Used)
The amount of the solvents used in the reaction of the present invention may be any amount as long as the reaction proceeds. From the viewpoints of yield, economic efficiency, etc., the range of 10 to 100 L (liter), preferably 20 to 50 L can be exemplified for 1 mol of the compound of formula (II) or the compound of formula (III), respectively. The amount of solvents used can be appropriately adjusted by those skilled in the art.
In the present specification, the pressurized state specifically means a range of pressure equal to or higher than the saturated vapor pressure with respect to the temperature of water. This can be achieved simply by charging the reaction solution in a closed batch reactor and setting a heating temperature. Therefore, a pressurized state close to the saturated vapor pressure is preferable in terms of pressure resistance and safety of the reactor.

(Reaction Temperature)

The reaction temperature of the present invention is not particularly limited as long as the reaction proceeds. From the viewpoints of yield, suppression of by-products, economic efficiency, etc., the range of 100° C. to 250° C., preferably 120° C. to 160° C., and more preferably 130° C. to 150° C. can be exemplified. However, the reaction temperature of the present invention can be appropriately adjusted by those skilled in the art.

(Reaction Time)

The reaction time of the present invention is not particularly limited. Those skilled in the art can obtain the cyclopentenone derivative represented by formula (I) in high yield by setting an optimum reaction time for each reaction temperature.

In the present invention, if the reaction conditions such as reaction temperature are appropriately selected, the compound of formula (I) can be obtained in high yield and high selectivity. Therefore, the aqueous solution containing the reaction product can be used as it is as a crude solution, or may be used as a crude material (paste) in which water is evaporated. In addition, in order to further improve the purity, it can be purified with a well-known method, if necessary. Examples of purification methods include chromatography, solvent extraction, re-precipitation, distillation and the like.

In conventional production methods that make full use of means of synthetic chemistry, since acids/alkalis, organic solvents, metals and halides are used as reactants and catalysts, products have to be actively separated and purified from the solution in which the compounds are mixed after reactions. Besides, neutralization and washing steps are generally essential. On the other hand, in the reaction step of the present invention, no acid/alkali is used, so that a neutralization step is not necessary. Besides, no organic solvent is used, so that a washing step for removing organic solvents is not necessary either. Even in the separation step, it is expected that use of an organic solvent or the like required for the separation can be suppressed due to high yield of products.

By using the cyclopentenone derivative represented by formula (I) as a starting material, it is possible to synthesize prostaglandin E1, pentenomycin (4R-4ß, 5ß-dihydroxy-5-hydroxymethyl-cyclopenten-1-one), dehydropentenomycin, xanthomycin, vertemycin (2-2-(hydroxyethoxy)-5-(hydroxymethyl)-1-cyclopentanone), and the like in fewer steps. Accordingly, there are great expectations for use as raw materials and reaction intermediates for medicines.

EXAMPLES

Hereinafter, the present invention will be described in more detail with reference to examples. However, the present invention is not limited to these examples.

Example 1

Water was added to tri-O-acetylglucal (II) (2.72 g, 10 mmol) to make the volume of 50 mL (0.2M). Then, heating (reaction) was started under pressure without evaporating the aqueous solution. The reaction temperature was set at 130° C. indicated by an autoclave device (Tomy Seiko, LSX-300) used for the reaction, and reacted for 18 hours. The reaction solution was filtered to remove solid components. The obtained yellow solution was poured into a column tube filled with synthetic resin SP207 (12.8 g), and then the reaction solution was repeatedly flowed until it became transparent. After it was eluted with 150 mL of water and the solvent was removed by distillation under reduced pressure, the residue was dissolved in 2-propanol. Then, hexane was added in double amount of 2-propanol, and the mixture was filtered through Celite to remove insoluble components. After removing the solvent by distillation under reduced pressure, the residue was purified with silica gel column chromatography (ethyl acetate/methanol=20/1). The compound of formula (I) was obtained as a pale-yellow oily substance.

$^1$H NMR (400 MHz, acetone-$d_6$); δ2.18 (dd, J=2.0, 18.4 Hz, 1H), 2.72 (dd, J=6.0, 18.4 Hz, 1H), 4.21 (s, 2H), 4.91-4.92 (m, 1H), 7.36-7.37 (m, 1H); $^{13}$C NMR (100 Mz, acetone-$d_6$); δ 45.9, 56.8, 68.6, 147.6, 157.7, 205.4 ppm; IR(neat); 1701, 3276 cm$^{-1}$; HR-MS (ESI-TOF): m/z calcd. for $C_6H_9O_3$ ([M+H]+), 129.0546; found, 129.0552.

Example 2

Tri-O-acetyl-D-glucal (2.72 g, 10 mmol) and sodium methoxide (27 mg, 0.5 mmol) were added and dissolved in 40 mL of methanol. After stirring for 1 hour, 400 μL of 1.25M HCl solution in methanol was added and stirred for 10 minutes to neutralize. The neutralized reaction solution was filtered using 5.44 g of neutral silica gel, and then eluted with 150 mL of methanol. The solvent was removed by distillation under reduced pressure to give D-glucal (III). The compound of formula (III) obtained was proceeded to the next reaction without purification. Water was added to D-glucal (III) to give an aqueous solution of (III). Further, water, hydrochloric acid and an aqueous solution of sodium hydroxide were used to adjust the pH to an arbitrary value, and the volume was adjusted to 50 mL (0.2M). Then, heating (reaction) was started under pressure without evaporating the aqueous solution. The reaction temperature was set at 130° C. indicated by an autoclave device (Tomy Seiko, LSX-300) used for the reaction. After a predetermined reaction time, the container was taken out and cooled to stop the reaction. The reaction solution was filtered to remove solid components. The yellow solution obtained was poured into a column tube filled with synthetic resin SP207 (12.8 g), and then the reaction solution was repeatedly flowed until it became transparent. After it was eluted with 150 mL of water and the solvent was removed by distillation under reduced pressure, the residue was dissolved in 2-propanol. Then, hexane was added in double amount of 2-propanol, and the mixture was filtered through Celite to remove insoluble components. After removing the solvent by distillation under reduced pressure, the residue was purified with silica gel column chromatography (ethyl acetate/methanol=20/1). The compound of formula (I) was obtained as a pale-yellow oily substance. A heating (reaction) under the same pressure was also conducted at the concentration of 0.8M. The analytical data of the compound of formula (I) obtained coincided with those in Example 1.

The results of the investigation on pH are shown in Table 1.

TABLE 1

Tri-O-acetyl-D-glucal (II) (2.72 g)
Concentration: 0.2M, reaction time: 18 hours,
reaction temperature: 130° C.

| pH | Solid component (mg) | Formula (I) (mg) | Yield (%) |
|---|---|---|---|
| 3 | 473 | 241 | 19 |
| 4 | 122 | 642 | 50 |
| 5 | 87 | 676 | 53 |
| 7 | 91 | 678 | 53 |
| 9 | 64 | 627 | 49 |

The results of the investigation on reaction time are shown in Table 2.

TABLE 2

Tri-O-acetyl-D-glucal (II) (2.72 g)
Concentration: 0.2M, pH: 5, reaction temperature: 130° C.

| Reaction time (h) | Solid component (mg) | Formula (I) (mg) | Yield (%) |
|---|---|---|---|
| 6 | 9 | 602 | 47 |
| 12 | 37 | 787 | 61 |
| 18 | 112 | 695 | 54 |
| 24 | 288 | 685 | 53 |

The results of the investigation on concentration are shown in Table 3.

TABLE 3

Tri-O-acetyl-D-glucal (II) (0.2M: 2.72 g, 0.8M: 10.88 g)
pH: 5, reaction time: 12 hours, reaction temperature: 130° C.

| Concentration (M) | Solid component (mg) | Formula (I) (mg) | Yield (%) |
|---|---|---|---|
| 0.2 | 37 | 787 | 61 |
| 0.8 | 1084 | 1967 | 38 |

INDUSTRIAL AVAILABILITY

In the production method for a cyclopentenone derivative according to the present invention, 4-hydroxy-2-hydroxymethyl-2-cyclopenten-1-one (the compound of formula (I)), which is useful as a medicine, an agricultural chemical, or a raw material or intermediate thereof, can be easily obtained after only one reaction step by heating and reacting a readily available compound of formula (II) (tri-O-acetyl-D-glucal) in water. In addition, in the production method for a cyclopentenone derivative according to the present invention, 4-hydroxy-2-hydroxymethyl-2-cyclopenten-1-one (the compound of formula (I)), which is useful as a medicine, an agricultural chemical, or a raw material or intermediate thereof, can be easily obtained after only two reaction steps by using inexpensive glucose as a starting material.

The materials used in the reaction are just tri-O-acetyl-D-glucal and an inexpensive solvent, which facilitates isolation. Especially when only water is used, the purification step can be omitted. Therefore, it is possible to industrially produce the cyclopentenone derivative represented by formula (I) at low cost. In addition, since the solvent used in the reaction is water and it is not necessary to use an organic solvent, it can be expected as a green process with low environmental stress. Furthermore, the starting material, tri-O-acetyl-D-glucal is a commercial product, and can be produced easily from inexpensive glucose that is naturally present in large amounts.

What is claimed is:

1. A production method for the compound represented by formula (I) comprising heating an aqueous solution of the compound represented by formula (II) as a starting material at 100 to 250° C. in a pressurized state without evaporation.

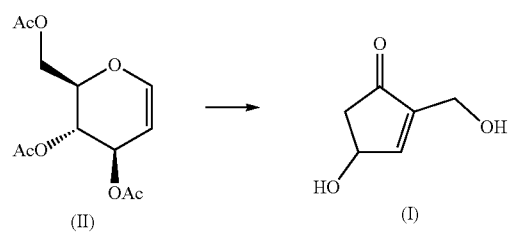 [SMILES: CC(=O)OC[C@H]1OC=C[C@@H](OC(C)=O)[C@@H]1OC(C)=O ; O=C1CC(O)C=C1CO ; "(I)" ; "(II)"]

2. A production method for the compound represented by formula (I) comprising heating an aqueous solution of the compound represented by formula (III) as a starting material at 100 to 250° C. in a pressurized state without evaporation.

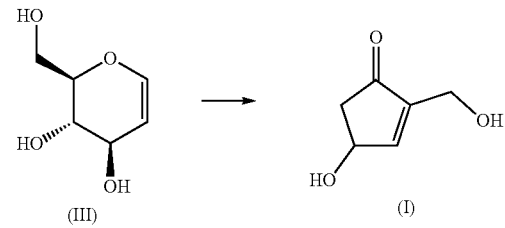 [SMILES: OC[C@H]1OC=C[C@@H](O)[C@@H]1O ; O=C1CC(O)C=C1CO ; "(III)" ; "(I)"]

3. The production method according to claim 1, wherein the concentration of the compound represented by formula (II) is in the range of 0.1 to 1.0M.

4. The production method according to claim 1, wherein the pH of the aqueous solution of the compound represented by formula (II) is in the range of 4 to 9.

5. The production method according to claim 2, wherein the concentration of the compound represented by formula (III) is in the range of 0.1 to 1.0M.

6. The production method according to claim 2, wherein the pH of the aqueous solution of the compound represented by formula (III) is in the range of 4 to 9.

* * * * *